United States Patent
Zheng et al.

(10) Patent No.: US 9,414,781 B2
(45) Date of Patent: Aug. 16, 2016

(54) THREE-DIMENSIONAL ULTRASONIC IMAGING SYSTEM

(71) Applicant: Telefield Medical Imaging Limited, Hong Kong (HK)

(72) Inventors: Yongping Zheng, Hong Kong (HK); Chung Wai James Cheung, Hong Kong (HK); Tak Man Mak, Hong Kong (HK); Cheong Lim Lee, Hong Kong (HK)

(73) Assignee: TELEFIELD MEDICAL IMAGING LIMITED, Hong Kong (HK)

( * ) Notice: Subject to any disclaimer, the term of this patent is extended or adjusted under 35 U.S.C. 154(b) by 54 days.

(21) Appl. No.: 14/416,639

(22) PCT Filed: Jul. 15, 2013

(86) PCT No.: PCT/CN2013/079385
§ 371 (c)(1),
(2) Date: Jan. 23, 2015

(87) PCT Pub. No.: WO2014/015747
PCT Pub. Date: Jan. 30, 2014

(65) Prior Publication Data
US 2015/0173668 A1  Jun. 25, 2015

Related U.S. Application Data

(60) Provisional application No. 61/674,400, filed on Jul. 23, 2012.

(30) Foreign Application Priority Data

Apr. 2, 2013 (CN) .......................... 2013 1 0113679

(51) Int. Cl.
| | |
|---|---|
| *A61B 5/00* | (2006.01) |
| *A61B 8/00* | (2006.01) |
| *A61B 8/08* | (2006.01) |
| *A61B 5/103* | (2006.01) |
| *A61B 5/11* | (2006.01) |

(52) U.S. Cl.
CPC ............. *A61B 5/4561* (2013.01); *A61B 5/1036* (2013.01); *A61B 8/4209* (2013.01); A61B8/4218 (2013.01); *A61B 8/4416* (2013.01); *A61B 8/4461* (2013.01); *A61B 8/483* (2013.01); *A61B 5/1121* (2013.01); *A61B 8/0875* (2013.01); *A61B 8/4245* (2013.01); *A61B 8/464* (2013.01)

(58) Field of Classification Search
None
See application file for complete search history.

(56) References Cited

U.S. PATENT DOCUMENTS

2011/0021914 A1*  1/2011  Zheng .................... A61B 5/103
600/443

FOREIGN PATENT DOCUMENTS

| CN | 201551326 U | 8/2010 |
| CN | 102497821 A | 6/2012 |
| WO | 2009021447 A1 | 2/2009 |

OTHER PUBLICATIONS

International Search Report of PCT Patent Application No. PCT/CN2013/079385 issued on Oct. 24, 2013.

*Primary Examiner* — Brian T Gedeon (57) ABSTRACT

A three-dimensional ultrasonic imaging system comprises a vertical stand (1), a computer (3), as well as an ultrasound scanner, a space sensor, and a first display (8) connected to the computer (3) respectively. The ultrasound scanner is provided with an ultrasonic probe (17). The three-dimensional ultrasonic imaging system further comprises a gravity balance board (2) mounted under the vertical stand (1) and connected to the computer (3), a second display (4) connected to the computer (3), and a support structure for supporting a patient. The support structure is mounted on an upper part of the vertical stand (1). The gravity balance board (2) is used to measure feet pressure distribution data information of the patient, and send the feet pressure distribution data information to the computer (3).

20 Claims, 5 Drawing Sheets

THREE-DIMENSIONAL ULTRASONIC IMAGING SYSTEM

TECHNICAL FIELD

The present application relates to the medical equipment field, in particular relates to a three-dimensional (3D) ultrasonic imaging system.

BACKGROUND

At present, spinal deformity can be assessed by a three-dimensional ultrasonic imaging procedure through a three-dimensional imaging system. The existing technology of three-dimensional ultrasonic imaging for spine generally requires patients to stand in an upright position with a natural and relaxed posture, which represents the normal stance and functional balance position. With this positioning, patients can be scanned by an ultrasonic probe for assessing the spinal deformity. Such positioning technique, however, is difficult to achieve good consistency between measurements during the follow-up, and thus may affect the outcome assessment for the treatment of spinal deformity. In addition, patients suffering from severe spinal deformity cannot stand in the required upright position with a natural and relaxed posture on the scanning platform for a long scanning time.

The body's centre of gravity can represent characteristics about body structure, shape, and mass distributing, thus it can provide useful reference data for medical rehabilitation fields and so on. During assessment of spinal deformity, the detection of the body's centre of gravity of patient can be used to evaluate the progression of spinal deformity and the treatment effectiveness. However, the conventional three-dimensional ultrasonic imaging system does not have such detection functions.

SUMMARY

An objective of the present application is to provide a three-dimensional ultrasonic imaging system which can facilitate to keep a patient standing with a natural and relaxed posture and to provide the detection of the body's centre of gravity of the patient, thus to overcome the difficulty of making the patient to keep standing in a required upright position when the existing three-dimensional imaging system is used to assess the spinal deformity assessment and its drawback of not detecting the body's centre of gravity of the patient.

According to one aspect, a three-dimensional ultrasonic imaging system is provided, which comprises a vertical stand, a computer, as well as an ultrasound scanner, a space sensor, and a first display connected to the computer respectively. The ultrasound scanner is provided with an ultrasonic probe. The three-dimensional ultrasonic imaging system further comprises a balance board mounted under the vertical stand and connected to the computer, a second display connected to the computer, and a support structure for supporting a patient. The support structure is mounted on an upper part of the vertical stand.

The gravity balance board is used to measure feet pressure distribution data information of the patient, and send the feet pressure distribution data information to the computer.

After processing the feet pressure distribution data information, the computer obtains feet position data information and feet gravity point position data information of the patient, and sends the feet pressure distribution data information, the feet position data information, and the feet gravity point position data information to the second display which displays same.

Advantageously, the gravity balance board further comprises a supporting board mounted on base of the vertical stand, a measuring board arranged on the supporting board, several pressure sensors mounted on the supporting board and contacted to the measuring board, and a data processing unit connected to the pressure sensors.

The pressure sensors are used to collect a pressure signal representing a load applied on the measuring board by two feet. The pressure signal is processed by the data processing unit to obtain the feet pressure distribution data information, and then sends the same to the computer.

Advantageously, the measuring board further comprises a first foot board and a second foot board around which several pressure sensors are distributed uniformly.

Advantageously, the three-dimensional ultrasonic imaging system further comprises an inputting device connected to the computer for inputting eye level information of the patient. The computer receives and processes the eye level information, and then shows the same via the second display.

Advantageously, the three-dimensional ultrasonic imaging system further comprises a first holder with height adjustable and mounted on the vertical stand. The second display is mounted on the first holder.

Advantageously, the vertical stand further contains a U-shape structure along the two sides of which, two sliding slots are arranged respectively in a vertical direction.

Advantageously, the support structure further comprises several supporters which are slideable along the sliding slots. Each of the supporters equips with a structure whose length is adjustable.

Advantageously, the support structure further comprises a first support plate and a second support plate which are moveably mounted in the sliding slots. The first support plate and second support plate are provided with two supporters, respectively.

Advantageously, the support structure further comprises several tracks, and two tracks are mounted on each sliding slot. Each track is installed with one supporter movable along it.

Advantageously, each of the supporters has a laser beam positioning device arranged inside.

Advantageously, the first support plate comprises a first plate body, a first sliding element arranged at the two ends of the first plate body respectively, and a first connecting hole for fixing the first plate body to the vertical stand. The second support plate comprises a second plate body, a second sliding element arranged at the two ends of the second plate body respectively, and a second connecting hole for fixing the second plate body to the vertical stand.

The first sliding element and the second sliding element are arranged inside and slideable along the sliding slot.

Advantageously, the three-dimensional ultrasonic imaging system further comprises a first motor and a second motor for driving the first support plate and the second support plate respectively to move upward or downward, a first lead screw connected to the first motor and a second lead screw connected to the second motor, wherein the first support plate is mounted on the first lead screw and the second support plate is mounted on the second lead screw.

Advantageously, a first array of inserting hole are further arranged symmetrically on left and right positions of the first support plate and a second array of inserting hole are arranged symmetrically on left and right positions of the second support plate as arrays. The supporter comprises a support head, a support body in threaded connection with the support head and a buckle via which the supporter is mounted in the inserting hole Advantageously, a first array of LED display device is further arranged corresponding to the first array of inserting hole, a second array of LED display device is arranged corresponding to the second array of inserting hole. When the supporters are installed inside the first array of inserting hole and the second array of inserting hole, the corresponding first array of LED display device and the corresponding second array of LED display device are activated to operate.

Advantageously, the three-dimensional ultrasonic imaging system further comprises a fasten belt installed on the vertical stand for fastening the patient.

Advantageously, the three-dimensional ultrasonic imaging system further comprises a mechanical arm mounted on the vertical stand, and the ultrasonic probe is mounted on a moveable part of the mechanical arm.

By using the three-dimensional ultrasonic imaging system according present application, following benefits can be obtained. When scanning the patient for spinal deformity diagnosis, the three-dimensional ultrasonic imaging system employs the support structure to support the patient, who must keep as steady as possible in a required upright position with a natural and relaxed posture during the scan, so that the diagnosis results can be accurate. In addition, the first support plate and the second support plate can record the mounting position of the supporter so as to facilitate the setting of the supporters during the next diagnosis. In such a way, consistency between different measurements can be achieved. Furthermore, the three-dimensional ultrasonic imaging system is capable of detecting the body's centre of gravity of the patient via the balance board, therefore the progression of the spinal deformity and the treatment effect can be determined according to the body's centre of gravity.

BRIEF DESCRIPTION OF THE DRAWINGS

Hereinafter, embodiments of present invention will be described in detail with reference to the accompanying drawings, wherein.

DETAILED DESCRIPTION OF THE PREFERRED EMBODIMENT

These technical features, objects and effects of present application will be better understood from the following description and drawings.

Figure 1:
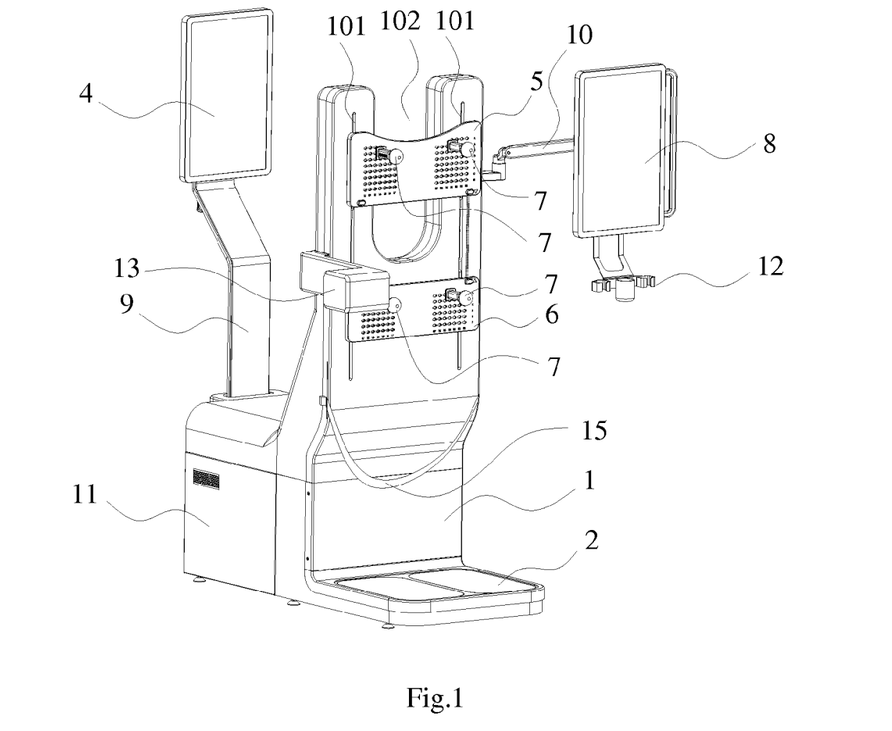
FIG. 1 is a structure diagram of the three-dimensional ultrasonic imaging system according to a first preferable embodiment of present application.

As shown in FIG. 1, the three-dimensional ultrasonic imaging system according to a first preferable embodiment of present application comprises a vertical stand 1, a gravity balance board 2, a computer 3, a second display 4, a first display 8, a support structure, an ultrasound scanner, as well as a space sensor.

The ultrasound scanner is provided with an ultrasonic probe 17 (shown in FIG. 9) connected to the computer 3. The space sensor comprises an electromagnetic transmitter 13 and an electromagnetic receiver (unshown). The electromagnetic transmitter 13 is mounted on the vertical stand 1 for generating a magnetic field in the space. It should be understood that, the electromagnetic transmitter 13 also can be mounted at other places, such as inside or around the support structure. In general, the electromagnetic receiver is connected to the ultrasonic probe 17 for detecting the intensity and amplitude change of the magnetic field. The space sensor is connected to the computer 3 for sending its space information to the computer 3 which then calculates the position and orientation of the ultrasonic probe 17 via a specific calculation method. The specific calculation method is a common known technology and not described here for concision. The first display 8 is connected to the computer 3 and finally shows the spine image of the patient after scanning the spine via the ultrasonic probe 17 and processing the scanning data via the computer 3.

The three-dimensional ultrasonic imaging system further comprises a second holder 10 via which the first display 8 is mounted on the vertical stand 1. The second holder 10 employs a structure whose length is adjustable. Accordingly, the mounting height of the first display 8 can be changed for adapting different users via adjusting the second holder 10.

Before the scanning, ultrasound gel is spread on the patient's body for covering the body area to be scanned. An object stage 12 provided with an ultrasound gel container is mounted under the first display 8 for placing the ultrasound gel, such that the operator can take out or put in the ultrasound gel conveniently. In the same way, the object stage 12 is also provided with an ultrasonic probe container for facilitating the operator to take out or put in the ultrasonic probe when scanning the patient.

The gravity balance board 2 is installed on the base of the vertical stand 1 and connected to the computer 3. When the patient stands on, the gravity balance board 2 measures the feet pressure distribution data and sends the same to the computer 3. After processing the feet pressure distribution data information, the computer 3 obtains feet position data information and feet gravity point position data information of the patient, and then sends the feet pressure distribution data information, the feet position data information, and the feet gravity point position data information to the second display 4 which receives and displays the same.

Figure 2:
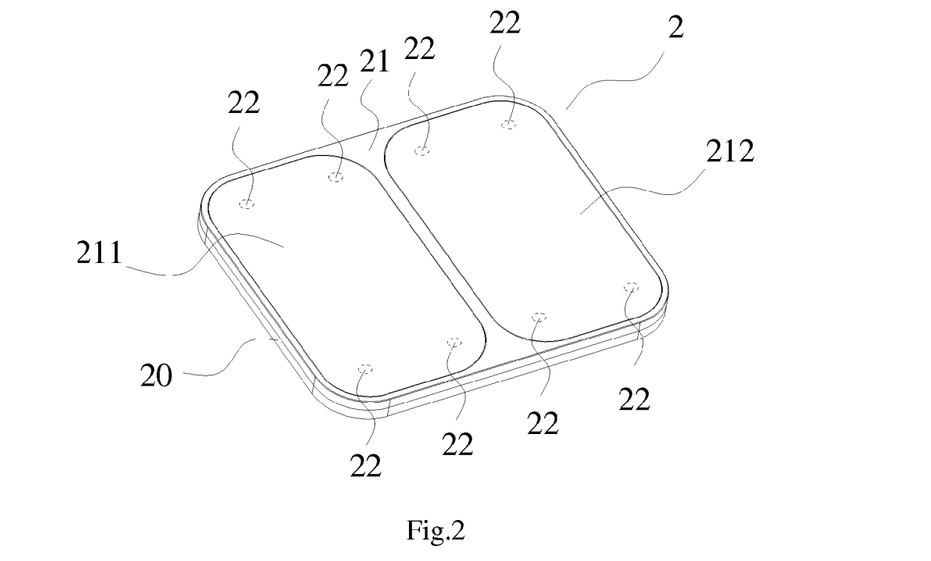
FIG. 2 is a structure diagram of the gravity balance board in the three-dimensional ultrasonic imaging system shown in FIG. 1.
Figure 3:
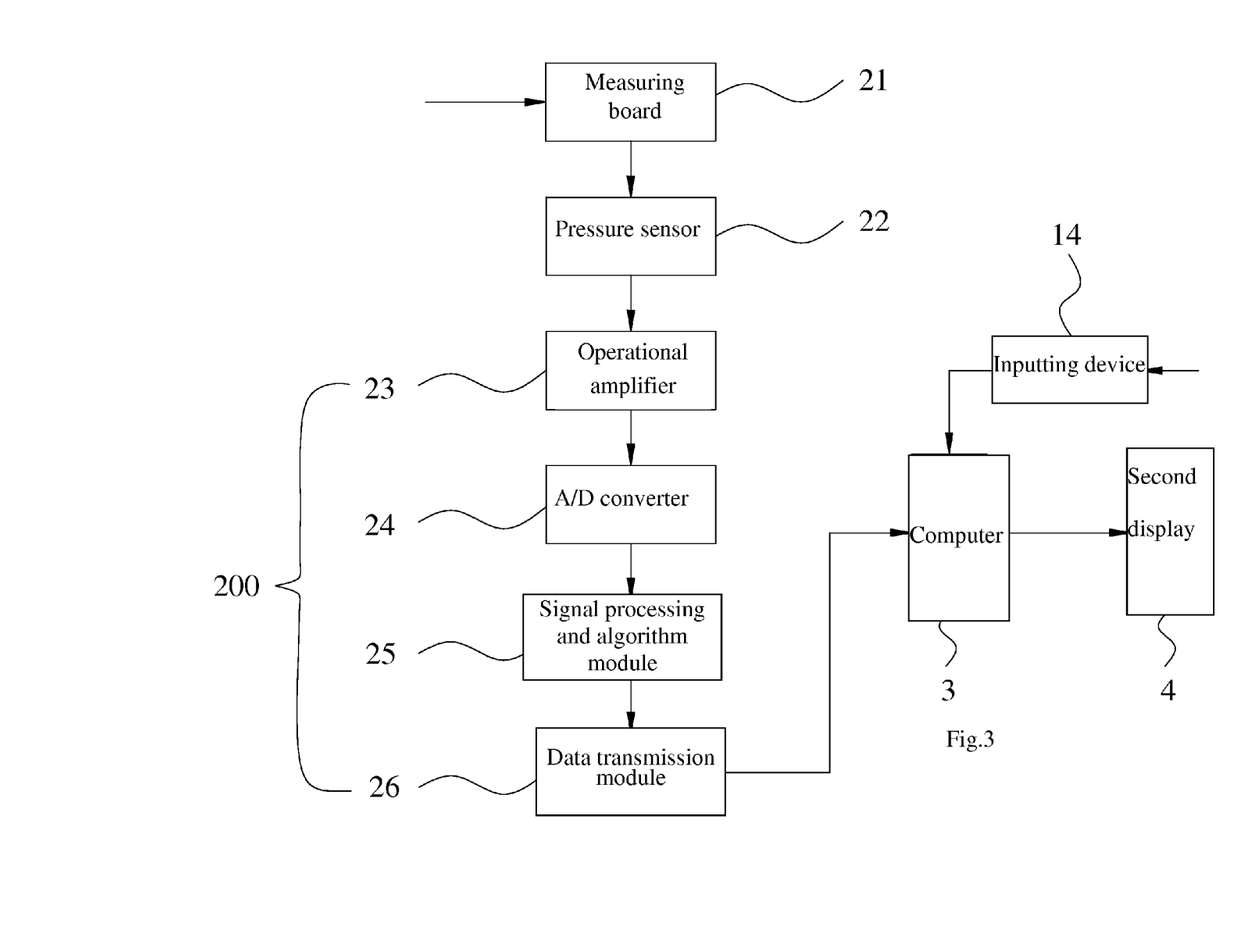
FIG. 3 is a block diagram showing the gravity centre mark and eye level mark of the patient in the three-dimensional ultrasonic imaging system shown in FIG. 1.

In the present embodiment, the gravity balance board 2 further comprises a supporting board 20, a measuring board 21, several pressure sensors 22 and a data processing unit 200. As shown in FIG. 2-3, the supporting board 20 is mounted on the vertical stand 1, and the measuring board 21 is arranged on the supporting board 20. Several pressure sensors 22 are mounted on the supporting board. In the present embodiment, eight pressure sensors 22 are distributed uniformly on the supporting board 20 and contact with the measuring board 21 to collect a pressure signal applied on the measuring board 21. After processing the pressure signal by the data processing unit 200, the feet pressure distribution data information of the patient is obtained and then sent to the computer 3.

In the present embodiment, the data processing unit 200 comprises an operational amplifier 23, an A/D converter 24, a signal processing and algorithm module 25 and a data transmission module 26. The operational amplifier 23 is connected to the pressure sensors 22 for receiving the pressure signal collected therefrom, and then filtering and amplifying the pressure signal. The A/D converter 24 is connected to the operational amplifier 23 for A/D converting the amplified pressure signal to a digital signal. The signal processing and algorithm module 25 is connected to the A/D converter 24 for algorithmic processing of the outputted digital signal, so as to obtain the feet pressure distribution data information of the patient. The data transmission module 26 is connected to the signal processing and algorithm module 25 for sending the feet pressure distribution data information to the computer 3 which obtains the feet position data information, and the feet gravity point position data information after receiving and processing the feet pressure distribution data information. Then, the computer 3 sends the feet pressure distribution data information, the feet position data information, and the feet gravity point position data information to the second display 4 which finally displays the same. The display content shown in the second display 4 may refer to FIG. 4. In order to observe the content displayed in the second display 4 conveniently and contrastively, a rectangular coordinate system 41 is pre-protracted via the computer 3. The feet pressure distribution image, the feet position image and the gravity center mark 42 are located in the rectangular coordinate system 41. The positions shown in the FIG. 4 indicate the offset between the gravity center of the body and the center of the rectangular coordinate system 41. The feet pressure distribution image can be marked by different colors for designating the pressure distribution of the two feet. When the patient stands on the gravity balance board 2 while shifting, the gravity center mark 42 moves along with the shifting of the patient in the rectangular coordinate system 41 correspondingly.

In the present embodiment, in order to guide the patient to stand at a proper position on the gravity balance board 2, the measuring board 21 comprises a first foot board 211 and a second foot board 212 which are arranged independently. Four pressure sensors are arranged under both of the first foot board 211 and the second foot board 212. In addition, the pressure sensors are distributed uniformly around the first foot board 211 and the second foot board 212 for measuring the pressure signals sensed by them. Meanwhile, the first foot board 211 and the second foot board 212 can also be used as marks for guiding the patient to stand at a proper position, in which the left foot is placed in the first foot board 211 and the right foot is place in the second foot board 212.

Figure 4:
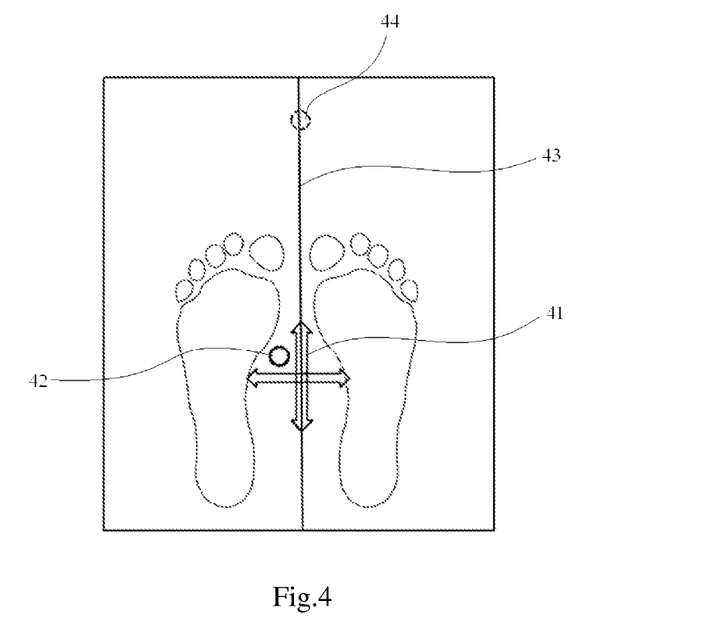
FIG. 4 is a diagram showing the display content of the second display in the three-dimensional ultrasonic imaging system shown in FIG. 1.

In the present embodiment, the three-dimensional ultrasonic imaging system further comprises an inputting device 14 for making the measured gravity center position data information more accurate. Referring FIG. 3, the inputting device 14 such as a keyboard and so on is connected to the computer 13. When the patient stands on the gravity balance board 2, a measuring tool measures the eye level height of the patient, and then inputs it to the computer 3 via the inputting device 14. After processing by the computer 13, the second display 4 shows the eye level height. FIG. 4 shows the display content of the second display 4. In order to observe the content displayed in the second display 4 intuitively, a central line 43 coincided with the Y-axis of the rectangular coordinate system 41 is pre-protracted via the computer 3. The eye level mark 44 obtained by the eye level height of the patient locates on the central line 43 and keeps consistent with the eye level height of the patient. During the measurement, the patient should keep the posture of staring the eye level mark 44 so as to limit the movement of the patient's head, thus enhancing the measurement accuracy of the body's center of gravity center position data information.

In present embodiment, the three-dimensional ultrasonic imaging system further comprises a first holder 9 with an adjustable height mounted on the vertical stand 1 for adapting the patient with different body shapes. The second display 4 is mounted on the first holder 9. The height of the second display 4 can be adjusted to a position where adapts the patient via adjusting the mounting height of the first holder 9. In one embodiment according to present application, the three-dimensional ultrasonic imaging system further comprises motors and lead screws which are connected to each other to drive the moving parts. The first holder 9 is mounted on the lead screw, so can be driven to move up or down via the lead screws by operating the motor. When the patient stands on the gravity balance board 2, the mounting height of the second display 4 can be adjusted according to the eye level height of the patient. Thus, the mounting height of the second display 4 can be adjusted via the structure comprising the motor, lead screw and the first holder 9.

In present embodiment, the support structure supporting the patient comprises a first support plate 5, a second support plate 6 and a supporter 7. The first support plate 5 and the second support plate 6 are mounted on the upper portion of the vertical stand 1. The first support plate 5 is mounted with two supporters 7 for supporting the clavicle frontal depression of the patient. The distance between the two supporters 7 can be adjusted according to the location of the clavicle frontal depression. The mounting location of the first support plate 5 on the vertical stand 1 is first determined according to the location of the clavicle frontal depression. Then the supporters 7 are mounted on the first support plate 5 such that they are against the clavicle frontal depression of the patient. In general, the two supporters 7 are arranged at the same height of the first support plate 5. However, when some patients have different heights for the left clavicle frontal depression and the right clavicle frontal depression, the two supporters 7 can be arranged at the different height of the first support plate 5 for supporting the clavicle frontal depression of the patient.

Similarly, the second support plate 6 is also mounted with two supporters 7 for supporting the anterior superior iliac spine of the patient. The distance between the two supporters 7 can be adjusted according to the location of the anterior superior iliac spine. The mounting location of the second support plate 6 on the vertical stand 1 is first determined according to the location of the anterior superior iliac spine. Then the supporters 7 are mounted on the second support plate 6 such that they are against the anterior superior iliac spine of the patient. The two supporters 7 can be arranged at the same or different heights of the second support plate 6 according to different patients.

The supporter 7 employs a structure whose length is adjustable, such that the patient can stand on the vertical stand 1 in an upstanding and relaxed posture. As the support structure comprising above the first support plate 5, the second support plate 6 and the supporter 7 is employed, the patient can stand on the vertical stand 1 with a natural and relaxed posture when scanning his body, thus the diagnosis results can be accurate. Meanwhile, as both the mounting position of the supporter 7 on the first support plate 5 and the second support plate 6, and the mounting positions of the first support plate 5 and the second support plate 6 on the vertical stand 1 can be adjusted, spine ultrasonic imaging requirements for patients having different body shapes are all satisfied.

In the present embodiment, the vertical stand 1 has a U-shape structure, that is, a U-shape notch 102 is arranged at the top middle of the vertical stand 1. Referring to FIG. 1, the U-shape notch 102 has a size adapt to different patients. When the patient stands on the gravity balance board 2 and faces the vertical stand 1, by which his eye level would not be obstructed.

Figure 6:
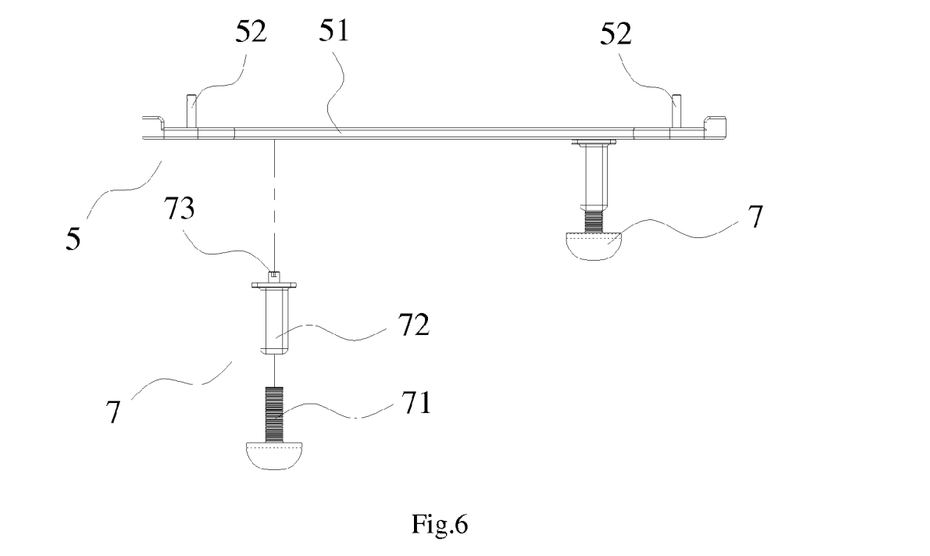
FIG. 6 is a top view of FIG. 5.
Figure 7:
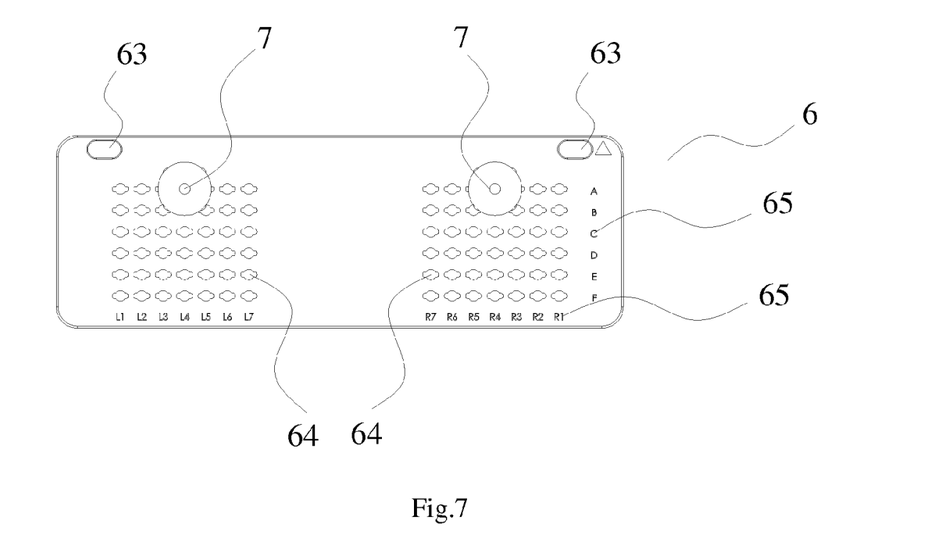
FIG. 7 is a diagram showing the connection between the second support plate and the supporter.
Figure 8:
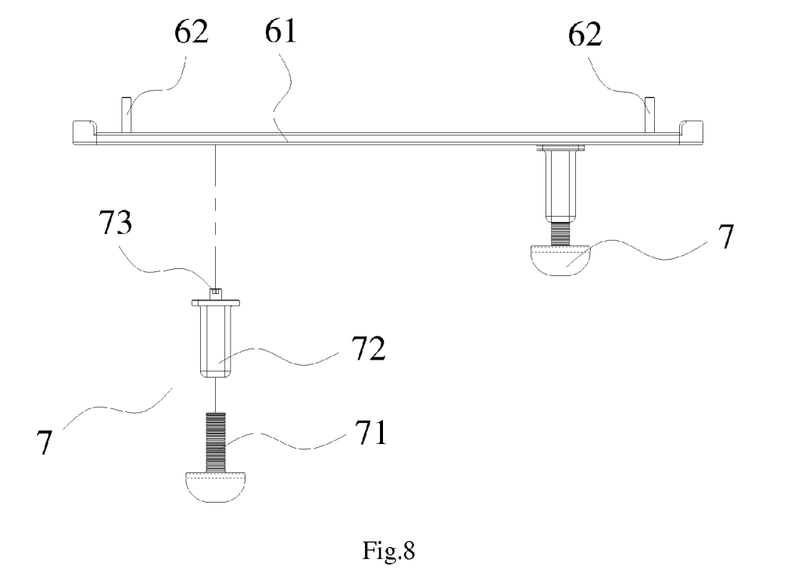
FIG. 8 is a top view of FIG. 7.

The vertical stand 1 has sliding slots 101 which are arranged along the two sides of the U-shape structure in a vertical direction respectively. Referring FIG. 1, the first support plate 5 comprises a first plate body 51 and a first sliding element 52. Referring FIG. 5-6, the first sliding element 52 is arranged at the two sides of the first plate body 51 respectively. Moreover, the first sliding element 52 is mounted and slideable in the sliding slot 101, such that the first support plate 5 can move up or down on the vertical stand 1. Similarly, the second support plate 6 comprises a second plate body 61 and a second sliding element 62. Referring FIG. 7-8, the second sliding element 62 is arranged at the two sides of the second plate body 61 respectively. Moreover, the second sliding element 62 is mounted and slideable in the sliding slot 101, such that the second support plate 6 can move up or down on the vertical stand 1. The first support plate 5 is provided with a first connecting hole 53 for fixing the first support plate 5 and the second support plate 6 to the vertical stand 1. Similarly, the second support plate 6 is provided with a second connecting hole 63. The three-dimensional ultrasonic imaging system further comprises several connecting elements which can be a screw element or a bolt element. The first support plate 5 is fixed on the vertical stand 1 via passing through the first connecting hole 53 by the connecting element. Similarly, the second support plate 6 is fixed on the vertical stand 1 via passing through the second connecting hole 63 by the connecting element. When moving the first support plate 5 or the second support plate 6, the user just needs to loose the fixed connection between the connecting elements and the vertical stand 1. In present embodiment, the first support plate 5 and the second support plate 6 are both connected with two connecting elements. It can be understood that, there can be more or less connecting elements.

In another embodiment, the three-dimensional ultrasonic imaging system comprises a first motor, a second motor, a first lead screw and a second lead screw. The first motor mounted on the vertical stand 1 connects with the first lead screw via its outputting shaft. The first support plate 5 is mounted on the first lead screw. The first motor drives the first support plate 5 to move up and down via the first lead screw. Similarly, the second motor mounted on the vertical stand 1 connects with the second lead screw via its outputting shaft. The second support plate 6 is mounted on the second lead screw. The second motor drives the second support plate 6 to move up and down via the second lead screw. The movements of the first support plate 5 and the second support plate 6 can be controlled automatically via controlling the movement of the first and second motors. In order to locate the movement position of the first support plate 5 and the second support plate 6 after moving up and down more accurately, the first and second motors are stepper motors. The first support plate 5 and the second support plate 6 can be arranged on the vertical stand 1 firmly by employing the structure comprising the first motor, the second motor, the first lead screw and the second lead screw.

In above embodiment, the first support plate 5 is provided with first inserting holes 54 arranged in arrays. Similarly, the second support plate 6 is provided with second inserting holes 64 arranged in arrays. The supporter 7 is provided with a buckle 73 via which the supporter 7 is mounted in the first inserting holes 54 and the second inserting holes 64, that is, the supporter 7 is mounted on the first support plate 5 and the second support plate 6. As the buckle connection can be disassembled easily, it is very convenient to adjust the mounting position of the supporter 7 on the first support plate 5 and the second support plate 6.

In order to mark the mounting positions of the supporter 7 on the first support plate 5 and the second support plate 6 respectively, a first LED display device 55 is arranged at each line and each row of the first inserting holes 54, and a second LED display device 65 is arranged at each line and each row of the second inserting holes 64 in the same way. When the supporter 7 are arranged inside the first inserting holes 54 and the second inserting holes 64 respectively, the first LED display device 55 and the second LED display device 65 are activated to operate for showing the location of the supporter 7 in the lines and rows. In present embodiment, the LED display portions in each line and each row of the first inserting holes 54 and the second inserting holes 64 are represented by different capital letters, such that the mounting position of the supporter 7 can be recorded expediently. For example, each line of the first inserting holes 54 and the second inserting holes 64 is represented by capital letters A, B, C, . . . and so on respectively, each row on the left of the first inserting holes 54 and the second inserting holes 64 is represented by capital letters L1, L2, L3 and so on respectively, and each row on the right of the first inserting holes 54 and the second inserting holes 64 is represented by capital letters R1, R2, R3 and so on respectively. The first LED display device 55 and the second LED display device 65 may record the mounting position of the supporter 7. When the patient returns, the supporter 7 can be mounted on the first support plate 5 and the second support plate 6 according to the last record. In such a way, the diagnostic time is save on one hand, and the treatment effect can be determined if the patient can not stand in a right posture one the other hand.

Figure 5:
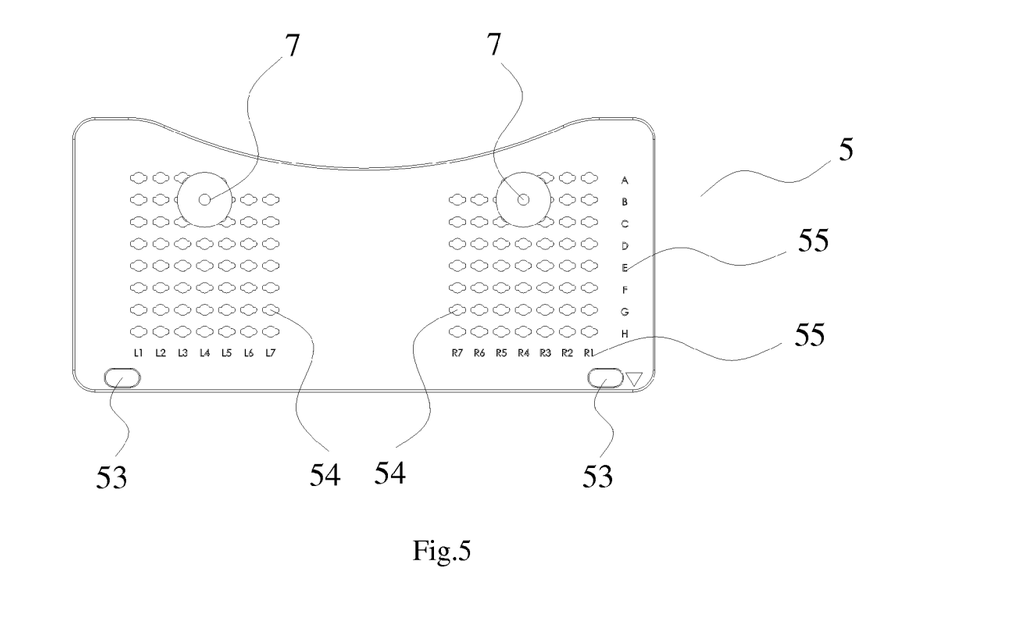
FIG. 5 is a diagram showing the connection between the first support plate and the supporter.

In above embodiment, the supporter 7 comprises a support head 71 with a screw on one side and a support body 72 arranged with a screw hole. The connection length between the support head 71 and the support body 72 can be adjusted via the screw connection, so that the supporter 7 is adjustable. The patient may stand on the vertical stand 1 in a standard upright position through adjusting the length of the supporter 7 according to his body shape. In another embodiment in which the length of the supporter 7 can be adjusted automatically, the supporter 7 comprises a support body, a motor connected to the support body, and a support head 71 driven by the motor. In this embodiment, the extending length of the supporter 7 can be adjusted via controlling the operation of the motor.

A laser beam positioning device is arranged on the supporter 7 for contacting with the clavicle frontal depression and anterior superior iliac spine of the patient more accurately. The supported parts of the supporter 7 on the patient, such as the clavicle frontal depression and anterior superior iliac spine, can be located accurately via the laser emitted by the laser beam positioning device.

A soft cushion is arranged at the other side of the support head 71 for making the patient feel comfortable when his body contacts the supporter 7. The soft cushion can relieve the pressure to the body from the supporter 7 and make the patient feel comfortable during the diagnostic process. In addition, the soft cushion can increase the friction between the patient and the supporter 7 which limits the movement of the patient during the scanning.

In present embodiment, the three-dimensional ultrasonic imaging system further comprises a fasten belt 15 arranged on the vertical stand 1 for fastening the patient. The mounting height and the extending length of the fasten belt 15 can be adjusted according to different patients. The fasten belt 15 also helps the patients who are seriously ill to keep standing and prevent them from tumbling.

In the above embodiment of present application, the three-dimensional ultrasonic imaging system further comprises a cabinet 11 for improving the integrality of present application. The cabinet 11 with the computer 13 arranged inside is mounted at the opposite side of the gravity balance board 2 on the vertical stand 1.

Figure 9:
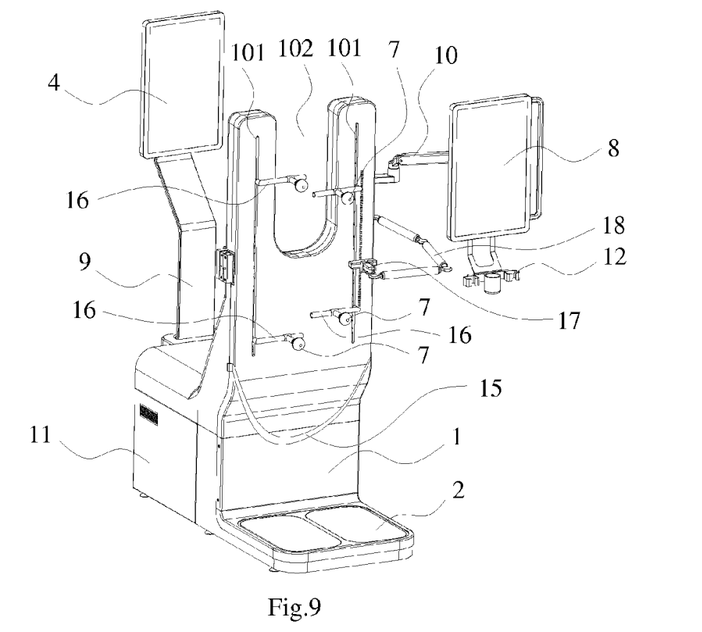
FIG. 9 is a structure diagram of the three-dimensional ultrasonic imaging system according to a second preferable embodiment of present application.

As shown in FIG. 9, the three-dimensional ultrasonic imaging system in the second preferable embodiment and that in the first preferable embodiment are different in the support structure. In present embodiment, the support structure further comprises several tracks 16 and several supporters 7. Two tracks 16 are mounted on each sliding slots 101 and slideable therein. The relative position of the four supporters 7 can be adjusted to supporting a proper location of the patient. By employing such support structure, the relative position of the four supporters 7 can be adjusted to support the patient at a proper location, so that the patient can stand on the vertical stand 1 with a natural and relaxed posture. In present embodiment, the motor can control the tracks 16 to move along the sliding slots 101 and the supporter 7 to move along the tracks 16. In such a way, the support portion of the supporter 7 on the patient can be located accurately via the laser emitted by the laser beam positioning device arranged inside the supporter 7 at first, and then the motor can adjust the relative position of the four supporters 7 automatically.

In the above embodiment of present application, the three-dimensional ultrasonic imaging system further comprises a mechanical arm 18 when referring FIG. 9. The mechanical arm 18 can be a common known mechanical arm mounted on the vertical stand 1 and has six degrees of freedom. The ultrasonic probe 17 is mounted on a moveable arm of the mechanical arm 18. The ultrasonic probe 17 can move in six degrees of freedom via controlling the movement of the mechanical arm 18. The ultrasonic probe 17 can be controlled to scan the patient's spine automatically via the mechanical arm 18, such that the doctor or operator has lower work strength and their operation fatigue is alleviated. Furthermore, the scan route of the ultrasonic probe 17 on the patient's spine can be controlled by pre-setting the movement trace of the mechanical arm 18. Again, by controlling the mechanical arm 18, the ultrasonic probe 17 scans the patient's spine in a steady speed which makes the detection results more accurate.

When implementing the above three-dimensional ultrasonic imaging system, the first support plate 5 and the second support plate 6 are fixed on the vertical stand 1 respectively according to the height of the clavicle and hip point on the patient. Then the supporters 7 are mounted on the first support plate 5 and the second support plate 6 respectively according to the body shape of the patient. Meanwhile, the length of the supporters 7 can be adjusted such that they are against the clavicle frontal depression of the patient. After that, the mounting height of the second display 4 can be adjusted according to the eye level of the patient, and the patient keeps the posture of staring the eye level mark 44 during the 3D ultrasonic imaging of his spine by the doctor. The second display 4 can display the gravity center mark 42 of the patient, so that the doctor can determine the progression of the spinal deformity and the treatment effect according to the body's centre of gravity of the patient. It can be understood that, the second display 4 can be mounted on the first holder 9. The patient's eye level and the eye level mark 44 can keep a certain position relationship therebetween through adjusting the position of the eye level mark 44.

When scanning the patient for spinal deformity diagnosis, the support structure comprising the first support plate 5, the second support plate 6 and the supporter 7 can support the patient, who must keep as steady as possible in a standard upright position with a natural and relaxed posture, so that the diagnosis results can be accurate. In addition, the support structure can be adjustable, so spine ultrasonic imaging requirements for patients having different body shapes are all satisfied. Furthermore, the balance board 2 can detecting the body's centre of gravity of the patient in a real time, the progression of the spinal deformity and the treatment effect can be determined according to the body's centre of gravity.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

The invention claimed is:

1. A three-dimensional ultrasonic imaging system comprising a vertical stand (1), a computer (3), as well as an ultrasound scanner, a space sensor, and a first display (8) connected to the computer (3) respectively, the ultrasound scanner is provided with an ultrasonic probe (17), wherein, the three-dimensional ultrasonic imaging system further comprises a gravity balance board (2) mounted under the vertical stand (1) and connected to the computer (3), a second display (4) connected to the computer (3), and a support structure for supporting a patient; wherein the support structure is mounted on an upper part of the vertical stand (1);

the gravity balance board (2) is used to measure feet pressure distribution data information of the patient, and send the feet pressure distribution data information to the computer (3);

after processing the feet pressure distribution data information, the computer (3) obtains feet position data information and feet gravity point position data information of the patient, and sends the feet pressure distribution data information, the feet position data information, and the feet gravity point position data information to the second display (4) which displays same.

2. The three-dimensional ultrasonic imaging system according to claim 1, wherein, the gravity balance board (2) comprises a supporting board (20) mounted on the vertical stand (1), a measuring board (21) arranged on the supporting board (20), several pressure sensors (22) mounted above the supporting board (20) and contacting the measuring board (21), a data processing unit (200) connected to the pressure sensors (22);

the pressure sensors (22) are used to collect a pressure signal sensed by the measuring board (21), after processing the pressure signal, the data processing unit (200) obtains the feet pressure distribution data information, and then sends the feet pressure distribution data information to the computer (3).

3. The three-dimensional ultrasonic imaging system according to claim 2, wherein, the measuring board (21) comprises a first foot board (211) and a second foot board (212) around which the several pressure sensors (22) are distributed uniformly.

4. The three-dimensional ultrasonic imaging system according to claim 3, wherein, the three-dimensional ultrasonic imaging system further comprises an inputting device (14) connected to the computer (3) for inputting eye level information of the patient, wherein the computer (3) receives and processes the eye level information, and then shows same via the second display (4).

5. The three-dimensional ultrasonic imaging system according to claim 4, wherein, the three-dimensional ultrasonic imaging system further comprises a first holder (9) with an adjustable height mounted on the vertical stand (1), and the second display (4) is mounted on the first holder (9).

6. The three-dimensional ultrasonic imaging system according to claim 1, wherein, the vertical stand (1) has a U-shape structure along two sides of which, a sliding slot (101) is arranged respectively in a vertical direction.

7. The three-dimensional ultrasonic imaging system according to claim 6, wherein, the support structure comprises several supporters (7) which are slideable along the sliding slot (101), each of the supporters (7) employs a structure whose length is adjustable.

8. The three-dimensional ultrasonic imaging system according to claim 7, wherein, the support structure further comprises a first support plate (5) and a second support plate (6) which are moveably mounted in the sliding slot (101), the first support plate (5) and second support plate (6) are provided with two of the supporters (7) respectively.

9. The three-dimensional ultrasonic imaging system according to claim 7, wherein, the support structure further comprises several tracks (16), and two of which are mounted on each of the sliding slot (101), each of the tracks (16) is provided with one of the supporters (7) movable along it.

10. The three-dimensional ultrasonic imaging system according to claim 7, wherein, each of the supporters (7) has a laser beam positioning device arranged inside.

11. The three-dimensional ultrasonic imaging system according to claim 8, wherein, each of the supporters (7) has a laser beam positioning device arranged inside.

12. The three-dimensional ultrasonic imaging system according to claim 9, wherein, each of the supporters (7) has a laser beam positioning device arranged inside.

13. The three-dimensional ultrasonic imaging system according to claim 8, wherein, the first support plate (5) comprises a first plate body (51), a first sliding element (52) arranged at two ends of the first plate body (51) respectively, and a first connecting hole (53) for fixing the first plate body (51) to the vertical stand (1), the second support plate (6) comprises a second plate body (61), a second sliding element (62) arranged at two ends of the second plate body (61) respectively, and a second connecting hole (63) for fixing the second plate body (61) to the vertical stand (1), wherein the first sliding element (52) and the second sliding element (62) are arranged inside and slideable along the sliding slot (101).

14. The three-dimensional ultrasonic imaging system according to claim 13, wherein, the three-dimensional ultrasonic imaging system further comprises a first motor and a second motor which driving the first support plate (5) and the second support plate (6) to move upward or downward respectively, a first lead screw connected to the first motor and a second lead screw connected to the second motor, wherein the first support plate (5) is mounted on the first lead screw and the second support plate (6) is mounted on the second lead screw.

15. The three-dimensional ultrasonic imaging system according to claim 13, wherein, several first inserting holes (54) are arranged symmetrically on left and right positions of the first support plate (5) as arrays and several second inserting holes (64) are arranged symmetrically on left and right positions of the second support plate (6) as arrays, the supporter (7) comprises a support head (71), a support body (72) in threaded connection with the support head (71) and a buckle (73) via which the supporter (7) is mounted in the first inserting holes (54) and the second inserting holes (64).

16. The three-dimensional ultrasonic imaging system according to claim 14, wherein, several first inserting holes (54) are arranged symmetrically on left and right positions of the first support plate (5) as arrays and several second inserting holes (64) are arranged symmetrically on left and right positions of the second support plate (6) as arrays, the supporter (7) comprises a support head (71), a support body (72) in threaded connection with the support head (71) and a buckle (73) via which the supporter (7) is mounted in the first inserting holes (54) and the second inserting holes (64).

17. The three-dimensional ultrasonic imaging system according to claim 15, wherein, a first LED display device (55) is arranged at each line and each row of the first inserting holes (54), a second LED display device (65) is arranged at each line and each row of the second inserting holes (64), when the supporters (7) are arranged inside the first inserting holes (54) and the second inserting holes (64), the first LED display device (55) and the second LED display device (65) is activated to operate.

18. The three-dimensional ultrasonic imaging system according to claim 16, wherein, a first LED display device (55) is arranged at each line and each row of the first inserting holes (54), a second LED display device (65) is arranged at each line and each row of the second inserting holes (64), when the supporters (7) are arranged inside the first inserting holes (54) and the second inserting holes (64), the first LED display device (55) and the second LED display device (65) is activated to operate.

19. The three-dimensional ultrasonic imaging system according to claim 1, wherein, the three-dimensional ultrasonic imaging system further comprises a fasten belt (15) arranged on the vertical stand (1) for fastening the patient.

20. The three-dimensional ultrasonic imaging system according to claim 1, wherein, the three-dimensional ultrasonic imaging system further comprises a mechanical arm (18) mounted on the vertical stand (1), on a moveable arm of which, the ultrasonic probe (17) is mounted.

\* \* \* \* \*